United States Patent [19]

Crossley

[11] 4,288,439

[45] Sep. 8, 1981

[54] ANTI-ULCER TREATMENT METHOD

[75] Inventor: Roger Crossley, Reading, England

[73] Assignee: John Wyeth & Brother Limited, Maidenhead, England

[21] Appl. No.: 98,418

[22] Filed: Nov. 29, 1979

[30] Foreign Application Priority Data

Nov. 30, 1978 [GB] United Kingdom ............... 46724/78

[51] Int. Cl.³ .............................................. A61K 31/44
[52] U.S. Cl. .................................................. 424/263
[58] Field of Search ...................................... 424/263

[56] References Cited

U.S. PATENT DOCUMENTS 3,121,088  2/1964  Jerchel et al. ....................... 546/261

FOREIGN PATENT DOCUMENTS 790069  7/1968  Canada ................................ 546/261

OTHER PUBLICATIONS

*Chim. Ther.*, 1966 (5–6) 337.
*Synthesis*, 1977, 884–885.

*Primary Examiner*—Frederick E. Waddell
*Attorney, Agent, or Firm*—George Tarnowski

[57] ABSTRACT

A method for treating ulcers or hypersecretion is described employing an anti-ulcer agent of formula I. Accordingly the invention provides a method for treating ulcers or hypersecretion in a mammal which comprises administering to said mammal an effective amount of an anti-ulcer agent of formula I

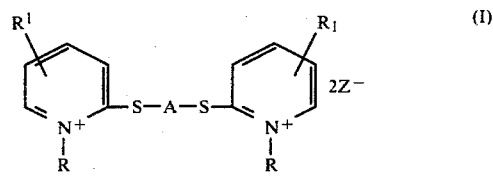

wherein R is alkyl of 1 to 6 carbon atoms or aralkyl of 7 to 12 carbon atoms, $R^1$ is hydrogen or alkyl of 1 to 6 carbon atoms, $Z^-$ is an anion selected from halide, lower alkyl- and arylsulphonate and the R and $R^1$ radicals may be the same or different, and A represents a methylene or ethylene radical optionally substituted by alkyl of 1 to 6 carbon atoms, oxo or hydroxy and S is sulphur.

Anti-ulcer compositions comprising a compound of formula I and a pharmaceutical carrier are also described.

3 Claims, No Drawings

ANTI-ULCER TREATMENT METHOD

The invention relates to a method for treating ulcers or hypersecretion involving certain known pyridinium compounds and pharmaceutical compositions for use in said method.

During the course of a search for novel anti-ulcer agents we have prepared and tested certain pyridinium compounds which have two pyridinium rings linked through two sulphur atoms and an alkylene chain. We have found that representative examples of this class of compounds possess anti-ulcer and/or anti-secretory activity. Some of these compounds are known but others are novel. So far as we are aware no specific pharmaceutical use for these compounds has previously been reported.

Accordingly the invention provides a method for treating ulcers or hypersecretion in a mammal which comprises administering to said mammal an effective amount of an anti-ulcer agent of formula I

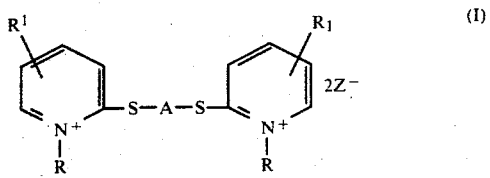

wherein R is alkyl of 1 to 6 carbon atoms or aralkyl of 7 to 12 carbon atoms, $R^1$ is hydrogen or alkyl of 1 to 6 carbon atoms, $Z^-$ is an anion selected from halide, lower alkyl- and arylsulphonate and the R and $R^1$ radicals may be the same or different, and A represents a methylene or ethylene radical optionally substituted by alkyl of 1 to 6 carbon atoms, oxo or hydroxy and S is sulphur.

The radical A is preferably methylene or ethylene.

In this specification the alkyl groups of 1 to 6 carbon atoms may be chosen from methyl, ethyl, n-propyl, isopropyl, n-butyl, s-butyl, t-butyl, n-pentyl and n-hexyl. The term aralkyl of 7 to 12 carbon atoms is intended to mean an alkyl group as discussed above substituted by phenyl.

$Z^-$ may be a halide ion e.g. chloride, bromide, iodide or fluoride or a lower alkyl- or arylsulphonate ion e.g. methane sulphonate or p-toluene sulphonate (tosyl).

The amount of compound used in the method will depend on the activity of the compound and the needs of the mammal being treated. Doses may range from 1 to 100 mg/kg.

Preferably the compound used is a methylene bis ((1-methylpyridinium-2-yl)-thio)dihalide or a 1,2-di-((1-methylpyridinium-2-yl)thio)ethane dihalide.

The invention includes a pharmaceutical composition in a form suitable for therapeutic administration comprising a compound of formula I and a pharmaceutically acceptable carrier. Preferably the pharmaceutical composition is in unit dosage form.

For the pharmaceutical carrier any suitable carrier known in the art can be used to prepare the pharmaceutical compositions. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

Anti-ulcer activity was determined by the stress-induced erosion test of Senay & Levine, Proc. Soc. Exp. Biol. Med., 124, 1221-3(1967) and anti-secretory activity by the test of H. Shay, D. Sun and H. Greenstein, Gastroenterology, 1954, 26,903-13 as exemplified by Beattie et al in J. Med Chem, 20,714 (1977). Compounds which possess one or both these activities are considered to be anti-ulcer agents which can be used for the treatment of ulcers or hypersecretion in mammals.

Some compounds of formula I are known, namely those in which $R^1$ is hydrogen, R is methyl, A is a polymethylene chain and Z is halogen. These compounds are described in Chim. Ther. 1966 (5–6), 337 mainly for their chemical interest. However, this publication does state that the compounds may exhibit possible pharmacological uses. I have found no reports of any tests having been carried out on these compounds. In view of the several hundreds of pharmacological tests which are available this statement is considered to be meaningless since it gives the reader no guidance as to what, if any, pharmacological activity the compounds might possess. Hence these compounds have not been described for use in any particular method of treatment of the human or animal body by surgery or therapy. The discovery that these compounds have anti-ulcer and/or anti-secretory activity which renders them useful for treatment of ulcers or hypersecretion in mammals is therefore the first therapeutical treatment application.

I have also found that compounds of formula I wherein A is propylene, butylene or pentylene are inactive as anti-secretory or anti-ulcer agents.

A few compounds of formula I wherein R is methyl, $R^1$ is hydrogen and A is ethylene substituted by phenethyl are disclosed as chemical intermediates in Synthesis, 1977, 884–885.

The compounds of formula I wherein $Z^-$ is a halide ion may be prepared by reacting a pyridothione of formula II

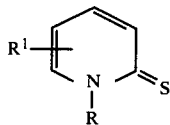

II wherein R and $R^1$ are as previously defined, with a dihaloalkylene compound of formula

Hal—A—Hal     III wherein Hal represents a halogen, which may be chlorine, bromine or iodine.

Alternatively a dipyridine compound of formula IV

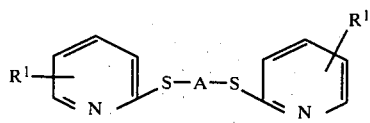

wherein $R^1$ and A are as defined in connection with formula I may be treated with an alkyl or aralkylating agent containing R and Z wherein R and Z are as defined in connection with formula I. For example the alkylating or aralkylating agent may be a lower alkyl or aralkyl halide or a lower alkyl or aryl sulphonic lower alkyl or aralkyl ester.

The invention is illustrated by the following examples.

EXAMPLE 1

Methylene bis((1-methylpyridinium-2-yl)-thio) diiodide

A solution of 1-methyl-2-pyridothione (2.5 g) in hot ethanol (20 ml) was added to di-iodomethane (0.81 ml). The mixture was heated under reflux for 3½ hours and then allowed to cool to room temperature. The resulting solid was removed by filtration and dried to give the title compound as a hemihydrate (4.7 g; 89%) mp 191°-3° C. (Found: C, 29.6; H, 3.3; N, 5.05% $C_{13}H_{16}I_2N_2S_2.\frac{1}{2}H_2O$ requires: C, 29.6; H, 3.25; N, 5.3%).

EXAMPLE 2

1,2-Di-((1-methylpyridinium-2-yl)thio)ethane dibromide

A solution of 1-methyl-2-pyridothione (1.25 g) in ethanol (10 ml) was treated with dibromoethane (0.43 ml). The mixture was heated under reflux for 6 hours and then allowed to cool to room temperature. The resulting solid was removed by filtration, washed with ether and dried to give the title compound as a hemihydrate (1.4 g; 63%) mp 204°-5.5° C. (Found: C, 37.3; H, 4.6; N, 6.0% $C_{14}H_{18}Br_2N_2S_2.\frac{1}{2}H_2O$ requires: C, 37.6; H, 4.3; N, 6.3%).

EXAMPLE 3

Methylene bis((1-methylpyridinium-2-yl)thio) ditosylate 2-(((2-pyridylthio)methyl)thio)pyridine is reacted with 2-molar equivalents of methyl tosylate at 100° C. to give the title compound.

EXAMPLE 4

Methylene bis((1-benzylpyridinium-2-yl)-thio)dichloride

Following the procedure of Example 3 but substituting benzylchloride for methyltosylate the title compound is prepared.

| | Pharmacological Test Results | | | |
|---|---|---|---|---|
| Compound [Product of Example No] | Stress Induced erosion (Senay & Levine) | | Anti-Secretory (Shay et al) | |
| | Dose mg/kg | % inhibition | Dose mg/kg | % change in volt |
| 1 | 100 | 71 | 30 | −62 |
| | | | 10 | −32 |
| 2 | 100 | 67 | 30 | −48 |

PHARMACEUTICAL COMPOSITIONS

The following examples illustrate the preparation of unit dosage form of pharmaceutical compositions according to the invention.

EXAMPLE A

| Antacid Tablet (chewable) | |
|---|---|
| Saccharin | 1.0 mg. |
| Hydrated alumina sucrose powder | 750.0 mg. |
| Methylene bis ((1-methylpyridinium-2-yl)thio) di-iodide | 100.0 mg. |
| Mannitol B.P. | 170.0 mg. |
| Maize starch B.P. dried | 30.0 mg. |
| Talc purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure. Triturate peppermint oil with talc (screen 40 mesh). Add the triturate, and other ingredients to a blender and mix thoroughly. Slug the powder to large hard slugs. Granulate the slugs through a 14 mesh screen. Compress the granules on a suitable compression machine to give tablets of the required size.

EXAMPLE B

| Anti-ulcer tablet (without antacid) | mg/tablet |
|---|---|
| 1,2-Di-((1-methylpyridinium-2-yl)thio)-ethane dibromide | 100 mg. |
| Celutab | 147.5 mg. |
| Mg. Stearate | 2.5 mg. |
| | 250.0 mg. |

The tablets are prepared by the following method. Blend the ingredients in a suitable blender. Compress the blended ingredients on a suitable compression machine to form tablets of the above composition. Celutab is a commercial product comprising 90–2% dextrose, 3–5% maltose, the remainder being higher glucose saccharides. The product is spray crystallised.

I claim:

1. A method for treating ulcers or hypersecretion in a mammal which comprises orally administering to said mammal an effective amount of an anti-ulcer agent of formula I

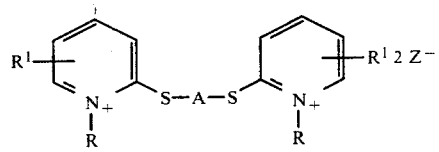

wherein R is alkyl of 1 to 6 carbon atoms, or aralkyl of 7–12 carbon atoms, $R^1$ is hydrogen or alkyl of 1 to 6 carbon atoms, and the R and $R^1$ radicals may be the same or different, A is methylene or ethylene radical, optionally substituted by lower alkyl of 1 to 6 carbon atoms, oxo, or hydroxy, S is sulphur and $Z^-$ is a halide or lower alkyl-or by aryl sulphonate anion.

2. A method as claimed in claim 1, wherein the compound of formula I is a methylene bis ((1-methylpyridinium-2-yl)-thio) dihalide.

3. A method as claimed in claim 1, wherein the compound of formula I is a 1,2-di((1-methylpyridinium-2-yl)thio)ethane dihalide.

* * * * *